US009595253B2

(12) United States Patent
Inoue

(10) Patent No.: US 9,595,253 B2
(45) Date of Patent: Mar. 14, 2017

(54) ACTIVE NOISE REDUCTION SYSTEM, AND VEHICULAR ACTIVE NOISE REDUCTION SYSTEM

(71) Applicant: HONDA MOTOR CO., LTD., Tokyo (JP)

(72) Inventor: Toshio Inoue, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/075,635

(22) Filed: Mar. 21, 2016

(65) Prior Publication Data

US 2016/0284337 A1 Sep. 29, 2016

(30) Foreign Application Priority Data

Mar. 24, 2015 (JP) ................................ 2015-061511
May 19, 2015 (JP) ................................ 2015-101922

(51) Int. Cl.
*A61F 11/06* (2006.01)
*G10K 11/16* (2006.01)
*H03B 29/00* (2006.01)
*G10K 11/178* (2006.01)

(52) U.S. Cl.
CPC ...... *G10K 11/1786* (2013.01); *G10K 2210/00* (2013.01); *G10K 2210/128* (2013.01);
(Continued)

(58) Field of Classification Search
CPC ........... G10K 11/1784; G10K 11/1786; G10K 11/1788; G10K 11/178; G10K 2210/1081;
(Continued)

(56) References Cited

U.S. PATENT DOCUMENTS 3,275,939 A * 9/1966 Luftig ...................... H04B 1/12 329/321
6,061,456 A * 5/2000 Andrea ................ G10K 11/178 381/71.13

(Continued)

FOREIGN PATENT DOCUMENTS

JP 7-30994 A 1/1995
JP 2001-056693 A 2/2001

(Continued)

OTHER PUBLICATIONS

Office Action dated Dec. 20, 2016, issued in counterpart Japanese Patent Application No. 2015-101922, with English translation. (6 pages).

*Primary Examiner* — Khai N Nguyen
(74) *Attorney, Agent, or Firm* — Westerman, Hattori, Daniels & Adrian, LLP

(57) ABSTRACT

A vehicular active noise reduction system includes a first microphone and first speaker disposed in a front-seat space, a second microphone and second speaker disposed in a back-seat space, and an active noise reduction device that performs control to output cancellation sound, to reduce noise in a cabin, from the first speaker and second speaker. When generating a first composite audio, the active noise reduction device removes audio components belonging to a frequency band relating to a second cancellation sound from audio collected by the first microphone, and when generating a second composite audio, removes audio components belonging to a frequency band relating to a first cancellation sound from audio collected by the second microphone.

8 Claims, 4 Drawing Sheets

(52) U.S. Cl.
CPC ................ *G10K 2210/1282* (2013.01); *G10K 2210/3025* (2013.01); *G10K 2210/3028* (2013.01); *G10K 2210/3055* (2013.01)

(58) Field of Classification Search
CPC ... G10K 2210/1282; G10K 2210/3025; G10K 2210/3028; G10K 2210/3055; H04R 1/1083
USPC ................................ 381/70, 71.1, 71.4, 94.1
See application file for complete search history.

(56) References Cited

U.S. PATENT DOCUMENTS

| | | | | | |
|---|---|---|---|---|---|
| 7,453,771 | B2 * | 11/2008 | Gatz | G10K 11/1788 | 367/127 |
| 7,533,759 | B2 * | 5/2009 | Krueger | F01N 1/065 | 181/206 |
| 7,542,575 | B2 * | 6/2009 | DeLine | B60R 1/12 | 381/122 |
| 7,853,026 | B2 * | 12/2010 | DeLine | B60R 1/12 | 381/122 |
| 8,184,828 | B2 * | 5/2012 | Christoph | G10L 21/0272 | 381/56 |
| 8,625,815 | B2 * | 1/2014 | DeLine | B60R 1/12 | 296/1.11 |
| 9,240,176 | B2 * | 1/2016 | Tzirkel-Hancock | G10K 11/002 | |
| 2007/0140060 | A1 * | 6/2007 | Gatz | G10K 11/1788 | 367/127 |
| 2014/0226831 | A1 * | 8/2014 | Tzirkel-Hancock | G10K 11/002 | 381/71.7 |

FOREIGN PATENT DOCUMENTS

| | | | |
|---|---|---|---|
| JP | 2002-51392 | A | 2/2002 |
| JP | 2002-514775 | A | 5/2002 |

* cited by examiner

ACTIVE NOISE REDUCTION SYSTEM, AND VEHICULAR ACTIVE NOISE REDUCTION SYSTEM

CROSS REFERENCES TO RELATED APPLICATIONS

The present application claims priority under 35 U.S.C. §119 to Japanese Patent Application No. 2015-101922, filed May 19, 2015, entitled "Active Noise Reduction System, and Vehicular Active Noise Reduction System." The contents of this application are incorporated herein by reference in their entirety.

TECHNICAL FIELD

The present disclosure relates to an active noise reduction system that assists conversation by actively suppressing noise in a closed space where cyclic noise occurs, and to a vehicular active noise reduction system.

BACKGROUND

There are known onboard acoustic devices for assisting smooth conversation within a closed space where cyclic noise occurs, such as in the cabin of a vehicle, for example (see Japanese Unexamined Patent Application Publication No. 2002-51392). The onboard acoustics device according to Japanese Unexamined Patent Application Publication No. 2002-51392 drives speakers disposed to the front of the vehicle cabin by a microphone disposed to the back of the vehicle cabin, and drives speakers disposed to the back of the vehicle cabin by a microphone disposed to the front of the vehicle cabin, thereby assisting smooth conversation among passengers in the front seat and the back seat.

On the other hand, there is also known active noise prediction technology, where cancellation sound having an antiphase as to the phase of the noise is generated from a speaker to reduce invasive noise to the cabin such as engine noise and the like, thereby actively reducing noise within the cabin (see Japanese Unexamined Patent Application Publication No. 7-30994).

However, attempting to apply a simple combination of the conversation assisting technology for within a closed space according to Japanese Unexamined Patent Application Publication No. 2002-51392 and the active noise reduction technology according to Japanese Unexamined Patent Application Publication No. 7-30994 results in a composite sound of the audio for conversation assistance and the cancellation sound for active noise reduction being output from the speaker. Since the active noise reduction technology according to Japanese Unexamined Patent Application Publication No. 7-30994 performs active noise reduction control based on the compounded sound picked up by a microphone, the behavior of this control may become unstable.

SUMMARY

The present application describes, for example, providing of an active noise reduction system that well copes with both conversation assistance in a closed space and active noise reduction.

A principal feature of a first aspect of the present disclosure is an active noise reduction system that actively reduces noise, including: a first sound collecting unit disposed in a first space in a closed space, that collects sound generated in the first space; a second sound collecting unit disposed in a second space situated away from the first space in the closed space, that collects sound generated in the second space; a first sound output unit that is disposed in the first space and outputs sound; a second sound output unit that is disposed in the second space and outputs sound; and an active noise reduction device that effects control to output a cancellation sound that reduces noise in the closed space, from at least one of the first sound output unit and the second sound output unit. The active noise reduction device includes a first audio compositing unit that generates first composite audio where audio signals of a first cancellation sound, generated by referencing the noise, and audio collected by the first sound collecting unit, are composited with audio collected by the second sound collecting unit, and a second audio compositing unit that generates second composite audio where audio signals of a second cancellation sound generated by referencing the noise, and audio collected by the second sound collecting unit, are composited with audio collected by the first sound collecting unit. The active noise reduction device effects control to output the first composite audio to the first sound output unit, while outputting the second composite audio to the second sound output unit, and at the time of generating the first and second composite audios, performs processing to remove audio components, belonging to a frequency band relating to noise that is to be reduced in the closed space, from each of the audio collected by the first sound collecting unit and the audio collected by the second sound collecting unit.

According to the first aspect, processing to remove audio components, belonging to a frequency band relating to noise that is to be reduced in the closed space, from each of the audio collected by the first sound collecting unit and the audio collected by the second sound collecting unit, is performed at the time of compositing audio signals of sound occurring in the first space and the second space with audio signals of cancellation sound relating to noise. Accordingly, conversation assistance from the front-seat passenger to the back-seat passenger in a closed space, and active noise reduction, both work correctly.

The active noise reduction device may further include a transfer function acquisition unit that acquires open-loop transfer functions of an acoustics system configured including the active noise reduction device, the first sound output unit and the second sound output unit, and the first sound collecting unit and the second sound collecting unit, a setting unit that sets a gain coefficient so that the open-loop transfer function acquired by the transfer function acquisition unit is 0 dB or smaller, and a correction unit that performs correction by multiplying each of error signals relating to sound collected at the first sound collecting unit and the second sound collecting unit by the gain coefficient set by the setting unit.

In a case where open-loop transfer functions of an acoustics system configured including the active noise reduction device, the first sound output unit and second sound output unit, and the first sound collecting unit and second sound collecting unit, includes frequency characteristics exceeding 0 dB (1 times), a reinforcing loop may be formed in the acoustics system resulting in the control operations relating to active noise reduction becoming unstable, which can lead to howling.

Accordingly, in the configuration above, the active noise reduction device includes a transfer function acquisition unit that acquires open-loop transfer functions of the acoustics system, a setting unit that sets a gain coefficient so that an open-loop transfer function acquired by the transfer function acquisition unit is 0 dB or smaller, and a correction unit that performs correction by multiplying each of error signals relating to sound collected at the first sound collecting unit and the second sound collecting unit by the gain coefficient set by the setting unit. According to this configuration, the correction unit performs correction of the error signals relating to the sound collected by the first sound collecting unit and second sound collecting unit, by multiplying by the gain coefficient that has been set, so stabilizing the control operations of active noise reduction enables a situation where howling occurs to be proactively avoided, and conversation assistance from the back-seat passenger to the front-seat passenger in a closed space and active noise reduction both work correctly.

The active noise reduction device may switchably have, as audio output modes used to output sound from at least one of the first sound output unit and the second sound output unit, a compounded sound output mode where the first composite audio is output to the first sound output unit while the second composite audio is output to the second sound output unit, and a cancellation sound output mode where the first or second cancellation sound is output from at least one of the first sound output unit and the second sound output unit. The active noise reduction device may further include a reference signal generating unit that generates a reference signal based on a standard signal correlated at least with the noise, a filter coefficient updating unit that updates a filter coefficient of the adaptive filter, using the reference signal generated at the reference signal generating unit, error signals related to sound collected by the first sound collecting unit or sound collected by the second sound collecting unit, and a step-size parameter set when adjusting coefficient updating amount of the adaptive filter, and a control signal generating unit that generates control signals relating to the first or second cancellation sounds by multiplying the standard signal by the filter coefficient of the adaptive filter. A value set to the step-size parameter in a case where the compounded sound output mode is selected may be smaller as compared to a case where the cancellation sound output mode is selected.

In a case where the compounded sound output mode is selected, control operations relating to active noise reduction may become unstable as compared to a case where the cancellation sound output mode is selected. The reason is that in the compounded sound output mode, the filter coefficient of the adaptive filter is updated in accordance with the results of sound collection relating to the first and second composite audios (error signals).

Accordingly, the value set to the step-size parameter in a case where the compounded sound output mode is selected is smaller as compared to a case where the cancellation sound output mode is selected. According to this configuration, stability of control operations relating to active noise reduction when updating the filter coefficient of the adaptive filters can be ensured, regardless of which of the compounded sound output mode and cancellation sound output mode is selected as the audio output mode.

The active noise reduction device may set a value larger than 0 but smaller than 1 as the gain coefficient in a case where the compounded sound output mode is selected, and on the other hand set 0 as the gain coefficient in a case where the cancellation sound output mode is selected. Switching from one of the compounded sound output mode and the cancellation sound output mode to the other audio output mode may be performed according to a predetermined time constant.

According to this configuration, a value larger than 0 but smaller than 1 is set as the gain coefficient in a case where the compounded sound output mode is selected, and on the other hand 0 is set as the gain coefficient in a case where the cancellation sound output mode is selected. Consequently, in a case where the compounded sound output mode is selected, correction is performed where the error signals relating to sound collected at the first sound collecting unit or second sound collecting unit are multiplied by a value larger than 0 but smaller than 1 as the gain coefficient. In this case, the influence of error signals can be suppressed. On the other hand, in a case where the cancellation sound output mode is selected, correction is performed where the error signals relating to sound collected at the first sound collecting unit or second collecting unit are multiplied by 0 as the gain coefficient. In this case, the influence of error signals can be eliminated. Further, switching from one of the compounded sound output mode or cancellation sound output mode to the other audio output mode is performed according to a predetermined time constant, so even in a case where the gain coefficients are switched in accordance with switching of the audio output mode, for example, occurrence of abnormal noise, which would occur in a case of having instantaneously (i.e., without a predetermined time constant) switched the audio output mode, can be suppressed.

A principal feature of a second aspect of the present disclosure is vehicular active noise reduction system that actively reduces noise, including: a first sound collecting unit disposed in a front-seat space in a cabin of a vehicle, that collects sound generated in the front-seat space; a second sound collecting unit disposed in a back-seat space in the cabin, that collects sound generated in the back-seat space; a first sound output unit that is disposed in the front-seat space and outputs sound; a second sound output unit that is disposed in the back-seat space and outputs sound; and an active noise reduction device that effects control to output a cancellation sound that reduces noise in the cabin, from at least one of the first sound output unit and the second sound output unit. The active noise reduction device includes a first audio compositing unit that generates first composite audio where audio signals of a first cancellation sound, generated by referencing the noise, and audio collected by the first sound collecting unit, are composited with audio collected by the second sound collecting unit, and a second audio compositing unit that generates second composite audio where audio signals of a second cancellation sound generated by referencing the noise, and audio collected by the second sound collecting unit, are composited with audio collected by the first sound collecting unit. The active noise reduction device effects control to output the first composite audio to the first sound output unit, while outputting the second composite audio to the second sound output unit, and at the time of generating the first and second composite audios, performs processing to remove audio components, belonging to a frequency band relating to noise that is to be reduced in the cabin, from each of the audio collected by the first sound collecting unit and the audio collected by the second sound collecting unit.

According to the second aspect, processing to remove audio components, belonging to a frequency band relating to noise that is to be reduced in the cabin, from each of the audio collected by the first sound collecting unit and the audio collected by the second sound collecting unit, is performed at the time of compositing sound occurring in the front-seat space and back-seat space in the cabin of the vehicle with cancellation sound relating to noise. Accordingly, conversation assistance in the vehicle cabin, and active noise reduction, both work correctly.

According to the active noise reduction system of the present disclosure, conversation assistance in a closed space and active noise reduction are both enabled to work correctly, by stabilizing control operations relating to active noise reduction.

BRIEF DESCRIPTION OF THE DRAWINGS

The advantages of the disclosure will become apparent in the following description taken in conjunction with the following drawings.

DETAILED DESCRIPTION

Figure 1:
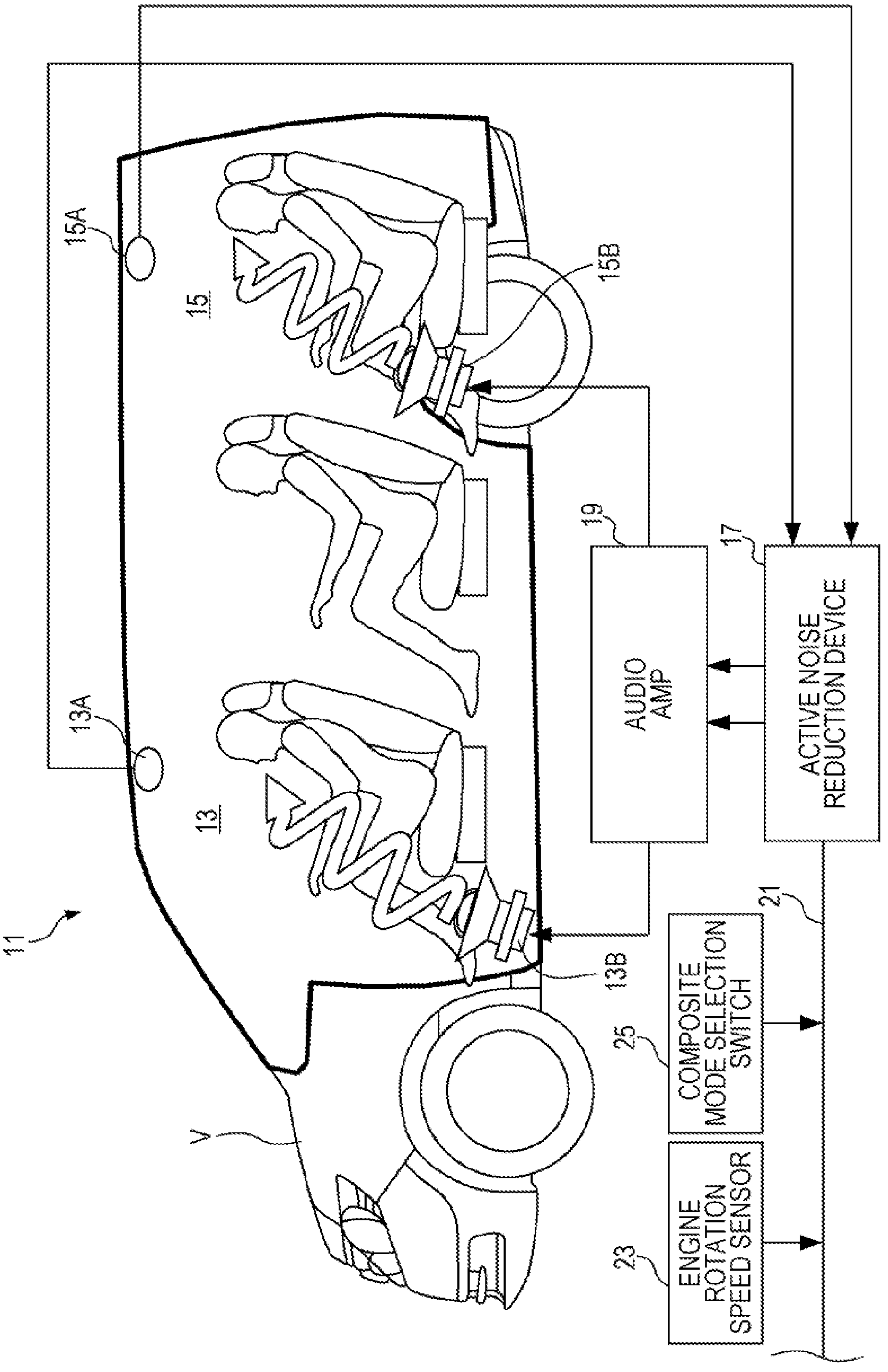
FIG. 1 is a schematic configuration diagram illustrating an example of an active noise reduction system according to embodiments of the present disclosure, installed in a vehicle.

An active noise reduction system according to first and second embodiments will be described in detail with reference to the drawings, by way of example of installation of the system in a vehicle. Note that in the description relating to the first and second embodiments, components that have the same functions between the two embodiments are denoted by the same reference numerals, as a rule. However, components which have the same functions between the two embodiments but also are unique to the first embodiment will be denoted by a suffix "−1", and those which are unique to the second embodiment will be denoted by a suffix "−2", as a rule. Further note that in a case where the active noise reduction system according to the first and second embodiments does not need individual description in the respective embodiments, the active noise reduction system will be denoted by reference numeral "11" with no suffixes, thereby collectively referring to the first and second embodiments. This is true regarding an active noise reduction device according to the first and second embodiments, as well.

Overview of Vehicular Active Noise Reduction System 11

First, an overview of the vehicular active noise reduction system 11 that is common to the first and second embodiments of the present disclosure will be described with reference to FIG. 1. FIG. 1 is a schematic configuration diagram illustrating an example of an active noise reduction system according to embodiments of the present disclosure, installed in a vehicle.

The vehicular active noise reduction system 11 according to the embodiments of the present disclosure functions to enable conversation assistance in the cabin of a vehicle V and active noise reduction to both work correctly. To realize this function, the vehicular active noise reduction system 11 includes a first microphone 13A disposed in a front-seat space 13 in the cabin of the vehicle V (hereinafter also referred to as "vehicle cabin") to collect sound, including human voice, generated in the front-seat space 13, a second microphone 15A disposed in a back-seat space 15 of the vehicle cabin to collect sound, including human voice, generated in the back-seat space 15, a first speaker 13B disposed in the front-seat space 13 to output sound, a second speaker 15B disposed in the back-seat space 15 to output sound, and an active noise reduction device 17 that effects control to output cancellation sound from at least one of the first speaker 13B and second speaker 15B, to reduce noise within the vehicle cabin, as illustrated in FIG. 1.

The front-seat space 13 corresponds to "first space" in the present disclosure, and the back-seat space 15 corresponds to "second space" in the present disclosure. The first microphone 13A corresponds to a "first sound collecting unit" in the present disclosure, and the second microphone 15A corresponds to a "second sound collecting unit" in the present disclosure. The first speaker 13B corresponds to a "first sound output unit" in the present disclosure, and the second speaker 15B corresponds to a "second sound output unit" in the present disclosure.

The active noise reduction device 17 is connected to an audio amplifier 19 that amplifies and outputs input audio signals, as illustrated in FIG. 1. The first speaker 13B and second speaker 15B are connected to output terminals (omitted from illustration) of the audio amplifier 19. The first speaker 13B and second speaker 15B transmit the sound of conversation in the vehicle cabin from one side to the other, and also serve to suppress noise in the vehicle cabin.

An engine rotation speed sensor 23 and a composite mode selection switch 25 are each connected to the active noise reduction device 17 via an information communication medium 21 such as a controller area network (CAN) for example, so as to be capable of communicating information, as illustrated in FIG. 1. A CAN is a multiplexed serial communication network used in general for information communication purposes among onboard devices, and has good data transfer speed and error detection capabilities. Note however, that the communication medium 21 used in the present disclosure is not restricted to a CAN. Another example of the communication medium 21 used in the present disclosure is FlexRay (a registered trademark).

The engine rotation speed sensor 23 functions to detect rotational speed of a reciprocating engine (omitted from illustration) mounted in the vehicle V. Engine rotation speed information detected by the engine rotation speed sensor 23 is sent to the active noise reduction device 17.

The composite mode selection switch 25 is a switch disposed within the vehicle cabin, operated by a passenger to select an audio output mode. Composite mode selection information selected at the composite mode selection switch 25 is sent to the active noise reduction device 17. Compounded sound output mode and cancellation sound output mode are audio output modes, which will be described later in detail.

Figure 2:
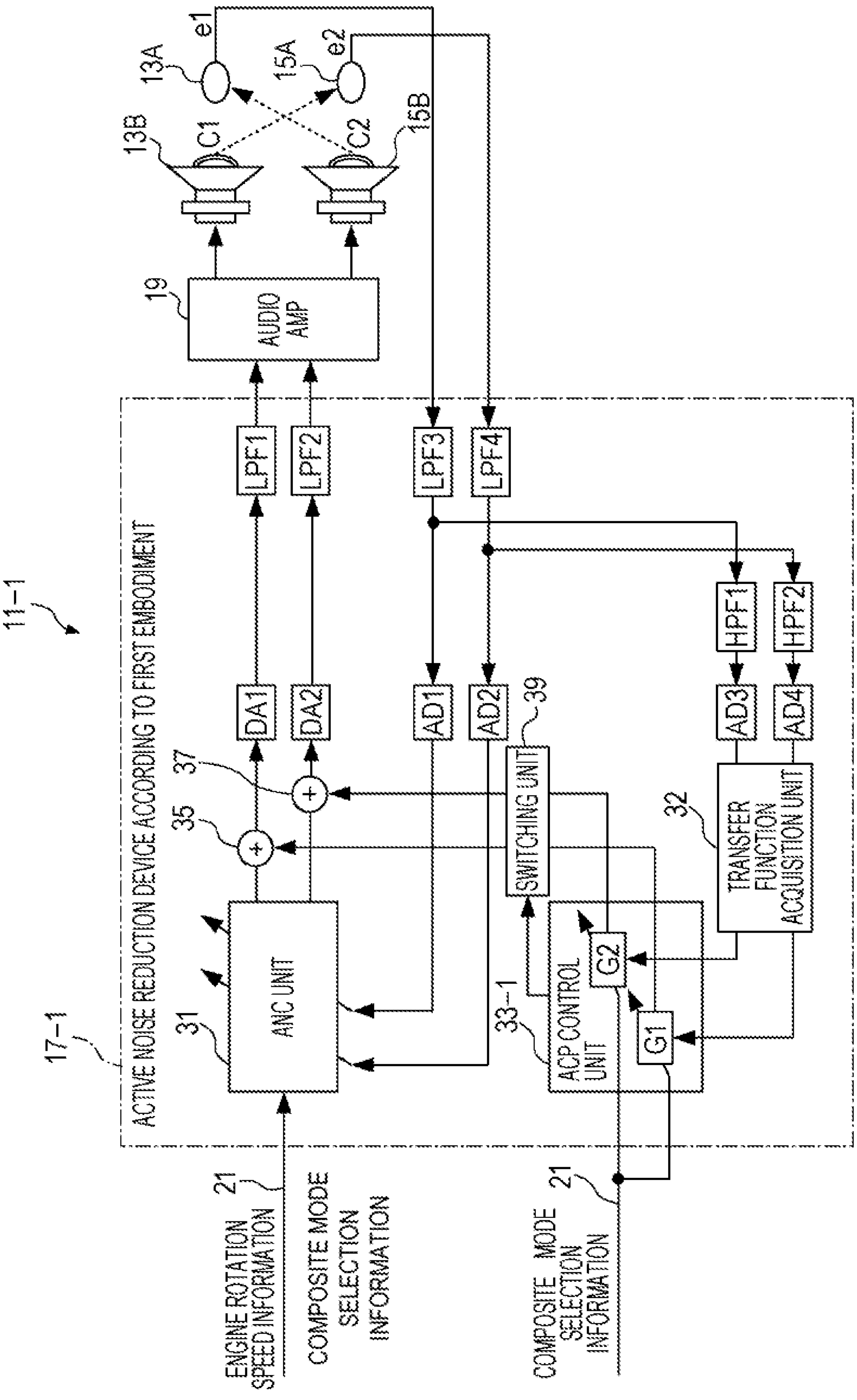
FIG. 2 is a block diagram schematically illustrating the internal configuration of an active noise reduction device according to a first embodiment.

Internal Configuration of Active Noise Reduction Device 17-1 According to First Embodiment First, the internal configuration of an active noise reduction device 17-1 according to the first embodiment will be described with reference to FIG. 2. FIG. 2 is a block diagram illustrating the schematics of the vehicular active noise reduction system 11-1 according to the first embodiment that has the active noise reduction device 17-1 according to the first embodiment. The active noise reduction device 17-1 according to the first embodiment is configured including an active noise control (ANC) unit 31, a transfer function acquisition unit 32, an active communication prompt (ACP) control unit 33-1, a first audio compositing unit 35, a second audio compositing unit 37, a first D/A converter DA1, a second D/A converter DA2, a first low-pass filter LPF1, a second low-pass filter LPF2, a third low-pass filter LPF3, a fourth low-pass filter LPF4, a first high-pass filter HPF1, a second high-pass filter HPF2, a first A/D converter AD1, a second A/D converter AD2, a third A/D converter AD3, a fourth A/D converter AD4, and a switching unit 39.

Specifically, the active noise reduction device 17-1 according to the first embodiment is configured as a microcomputer including, for example, a central processing unit (CPU), read only memory (ROM), random access memory (RAM), and so forth.

The ANC unit 31 is configured as a functional unit of the microcomputer. The microcomputer reads out and executes programs stored in the ROM, to carry out execution control of noise reduction functions of the ANC unit 31, and so forth.

The transfer function acquisition unit 32 is configured as a functional unit of the microcomputer. The microcomputer reads out and executes programs stored in the ROM, to carry out execution control of later-described open-loop transfer function acquisition functions of the transfer function acquisition unit 32, and so forth.

The ACP control unit 33-1 is configured as a functional unit of the microcomputer. The microcomputer reads out and executes programs stored in the ROM, to carry out execution control of conversation assistance functions of the ACP control unit 33-1, and so forth.

The active noise reduction device 17 has a function of generating first cancellation sound audio signals by referencing the engine sound (engine rotation speed information) and an error signal e1 related to sound collected by the first microphone 13A, for example, as illustrated in FIG. 2. This function is realized by the ANC unit 31. The active noise reduction device 17 also has a function of generating second cancellation sound audio signals by referencing the engine sound (engine rotation speed information) and an error signal e2 related to sound collected by the second microphone 15A, for example, as illustrated in FIG. 2. This function is also realized by the ANC unit 31.

That is to say, the ANC unit 31 serves to reduce noise in the vehicle cabin by performing control to output first and second cancellation sounds from the first speaker 13B and second speaker 15B, respectively. The first and second cancellation sounds are for reducing noise in the vehicle cabin (including noise generated in the vehicle cabin and noise of the engine and the like, for example, transmitted from outside of the vehicle cabin). The ANC unit 31 also serves to set the value of a step-size parameter set at the time of adjusting operation stability of adaptive filters (see first adaptive filter 47A and second adaptive filter 47B in FIG. 3), based on composite mode selection information according to the composite mode selection switch 25. The detailed configuration of the ANC unit 31 will be described later in detail.

The active noise reduction device 17 also has a function of generating first composite audio where the first cancellation sound audio signal, generated at the ANC unit 31 for canceling out noise occurring at the front-seat space 13, is composited with the error signal e2 relating to the conversation voice of a passenger in the back seat, collected by the second microphone 15A, as illustrated in FIG. 2. This function is also realized by the first audio compositing unit 35.

The active noise reduction device 17 also has a function of generating second composite audio where second cancellation sound audio signals, generated at the ANC unit 31 for canceling out noise occurring at the back-seat space 15, is composited with the error signal e1 relating to the conversation voice of a passenger in the front seat, collected by the first microphone 13A, as illustrated in FIG. 2. This function is also realized by the second audio compositing unit 37.

The active noise reduction device 17 also has a function of removing sound components belonging to frequency bands according to noise in the vehicle cabin to be reduced, from the error signal e1 relating to sound collected by the first microphone 13A and the error signal e2 relating to sound collected by the second microphone 15A, respectively, at the time of generating the first and second composite audios. These functions are realized by the first high-pass filter HPF1 and the second high-pass filter HPF2, respectively.

As illustrated in FIG. 2, the active noise reduction device 17-1 according to the first embodiment has a function of acquiring a first transfer function C1 relating to a path from the first speaker 13B to the second microphone 15A, and a second transfer function C2 relating to a path from the second speaker 15B to the first microphone 13A. The function of acquiring the first and second transfer functions C1 and C2 is realized by measuring the first and second transfer functions C1 and C2 beforehand, for example.

The active noise reduction device 17-1 according to the first embodiment functions to acquire open-loop transfer functions, as an overall acoustics system (acoustic signal feedback group) configured including the active noise reduction device 17-1, first speaker 13B and second speaker 15B, first microphone 13A and second microphone 15A, and audio amplifier 19 (although the audio amplifier 19 may be omitted), as illustrated in FIG. 2. This open-loop transfer function acquisition function is realized by the transfer function acquisition unit 32 that outputs measurement signals, and measures open-loop transfer functions as to the measurement signals, as the overall acoustics system. The transfer function acquisition unit 32 corresponds to a "transfer function acquisition unit" in the present disclosure. The acoustics system is thus configured including the audio amplifier 19 that drives the first speaker 13B and second speaker 15B, and the acoustic space from the first speaker 13B or second speaker 15B to the first microphone 13A or second microphone 15A. The precision of the open-loop transfer functions is improved by acquiring open-loop transfer functions as the overall acoustics system.

The ACP control unit 33-1 of the active noise reduction device 17-1 according to the first embodiment sets gain coefficients G1 and G2 so that the open-loop transfer function is 0 dB (1 times) or smaller at all frequency bands. The ACP control unit 33-1 corresponds to a "setting unit" in the present disclosure.

The active noise reduction device 17-1 according to the first embodiment has a function to perform correction where the error signal e1, relating to the conversation voice of the passenger in the front seat collected by the first microphone 13A, is multiplied by the gain coefficient G2 set as described above, and a function to perform correction where the error signal e2, relating to the conversation voice of the passenger in the back seat collected by the second microphone 15A, is multiplied by the gain coefficient G1 set as described above, as illustrated in FIG. 2. These functions are realized by the ACP control unit 33-1. The ACP control unit 33-1 corresponds to a "correction unit" in the present disclosure. The ACP control unit 33-1 thus configured serves to smoothly transmit voice of conversation in the vehicle cabin from one side to the other side.

The first D/A converter DA1 converts first composite audio that has been generated in digital signal format at the first audio compositing unit 35 into analog signal format, and outputs to the first low-pass filter LPF1. The second D/A converter DA2 converts second composite audio that has been generated in digital signal format at the second audio compositing unit 37 to into analog signal format, and outputs to the second low-pass filter LPF2.

The first low-pass filter LPF1 passes, of the frequency bands of the first composite audio that is in analog signal format, audio signals of frequency bands lower than a cutoff frequency that is set as appropriate, such as 200 Hz or the like, and outputs to the audio amplifier 19. The second low-pass filter LPF2 passes, of the frequency bands of the second composite audio that is in analog signal format, audio signals of frequency bands lower than the cutoff frequency, and outputs to the audio amplifier 19. The first low-pass filter LPF1 and second low-pass filter LPF2 here function as reconstruction filters that reconstruct the first and second composite audio in analog signal format. The analog signal waveforms exhibited by the first and second composite audio are thus formed smoothly.

The third low-pass filter LPF3 passes, of the frequency bands of the analog error signal e1 relating to the sound collected by the first microphone 13A, audio signals of frequency bands lower than a cutoff frequency that is set as appropriate, such as 200 Hz or the like, and outputs to the first A/D converter AD1 and first high-pass filter HPF1. The fourth low-pass filter LPF4 passes, of the frequency bands of the analog error signal e2 relating to the sound collected by the second microphone 15A, audio signals of frequency bands lower than the cutoff frequency, and outputs to the second A/D converter AD2 and second high-pass filter HPF2. The third low-pass filter LPF3 and the fourth low-pass filter LPF4 serve as anti-aliasing filters to satisfy the sampling theorem. The cutoff frequency of the third low-pass filter LPF3 and the fourth low-pass filter LPF4 accordingly is set to ½ of the sampling frequency of the micro-computer making up the ANC unit 31 and the ACP control unit 33-1 or lower. Thus, the computation processing load on the active noise reduction device 17 can be reduced by configuring the third low-pass filter LPF3 and the fourth low-pass filter LPF4 using analog filter circuits.

The first A/D converter AD1 converts the analog error signal e1 following low-pass filter processing at the third low-pass filter LPF3 into a digital error signal e1, and outputs to the ANC unit 31. The second A/D converter AD2 converts the analog error signal e2 following low-pass filter processing at the fourth low-pass filter LPF4 into a digital error signal e2, and outputs to the ANC unit 31.

The first high-pass filter HPF1 passes, of the analog error signal e1 that has been subjected to low-pass filter processing at the third low-pass filter LPF3, audio signals of a frequency band higher than a cutoff frequency that is set as appropriate, such as 200 to 300 Hz or the like, and outputs to the third A/D converter AD3. The second high-pass filter HPF2 passes, of the analog error signal e2 that has been subjected to low-pass filter processing at the fourth low-pass filter LPF4, audio signals of a frequency band higher than the cutoff frequency, and outputs to the fourth A/D converter AD4. Thus, the computation processing load on the active noise reduction device 17 can be reduced by configuring the first high-pass filter HPF1 and the second high-pass filter HPF2 using analog filter circuits.

The third A/D converter AD3 converts the analog error signal e1 that has been subjected to high-pass filter processing at the first high-pass filter HPF1 into a digital error signal e1, and outputs to the ACP control unit 33-1 via the transfer function acquisition unit 32. The fourth A/D converter AD4 converts the analog error signal e2 that has been subjected to high-pass filter processing at the second high-pass filter HPF2 into a digital error signal e2, and outputs to the ACP control unit 33-1 via the transfer function acquisition unit 32.

The switching unit 39 has a function of switching the audio output mode for output sound from at least one of the first speaker 13B and the second speaker 15B to one or the other of the compounded sound output mode and cancellation sound output mode, based on the composite mode selection information according to the composite mode selection switch 25. The compounded sound output mode is a mode where the composite signals are output as compounded sound. In the compounded sound output mode, the active noise reduction device 17 outputs first compounded sound from the first speaker 13B while outputting second compounded sound from the second speaker 15B. In the cancellation sound output mode, the active noise reduction device 17 outputs first cancellation sound from the from the first speaker 13B while outputting second cancellation sound from the second speaker 15B.

Internal Configuration of ANC Unit 31

Figure 3:
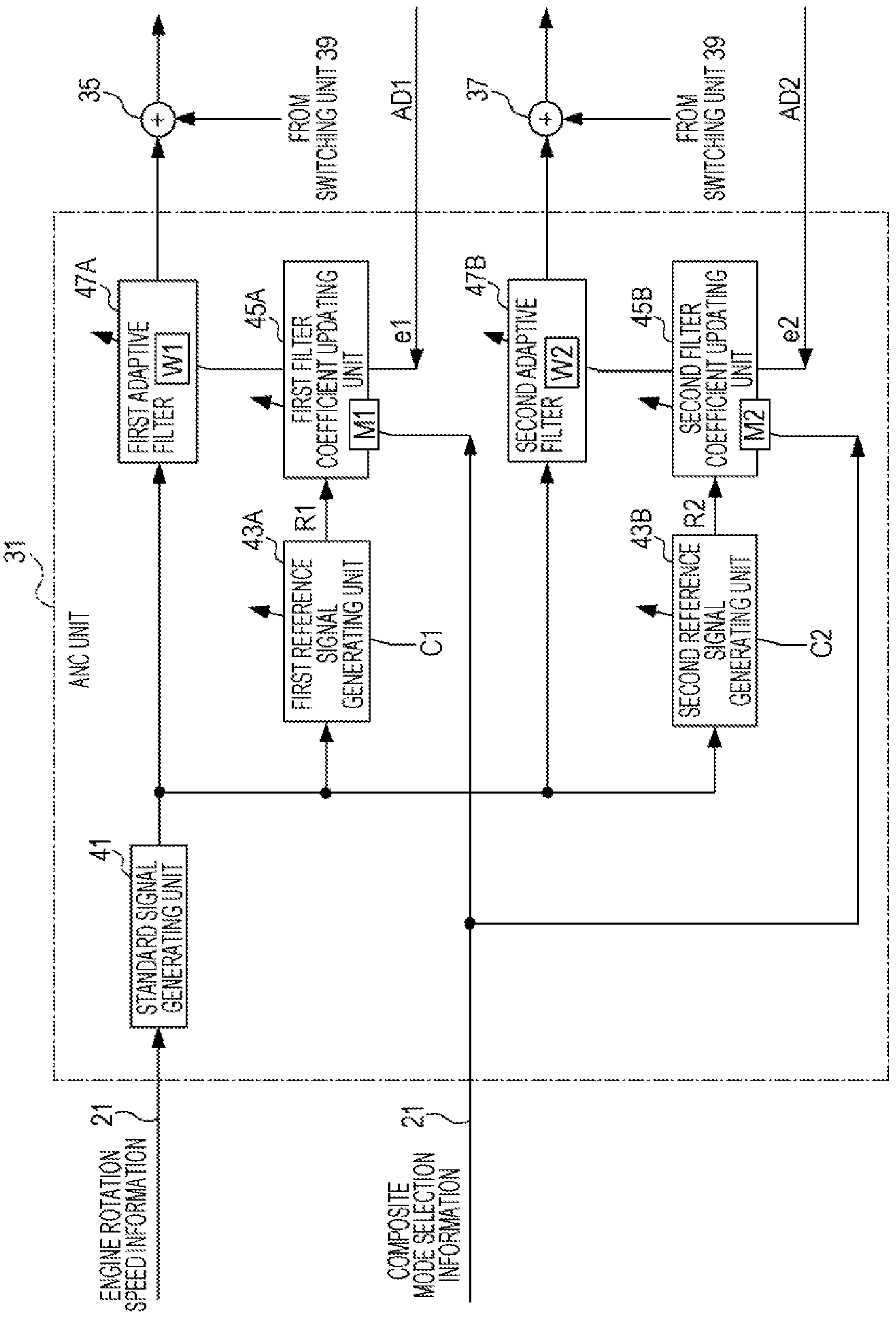
FIG. 3 is a block diagram schematically illustrating the internal configuration of an active noise control (ANC) unit.

Next, the internal configuration of the ANC unit 31 will be described with reference to FIG. 3. FIG. 3 is a block diagram schematically illustrating the internal configuration of the ANC unit 31. As illustrated in FIG. 3, the ANC unit 31 is configured including a standard signal generating unit 41, a first reference signal generating unit 43A, a second reference signal generating unit 43B, a first filter coefficient updating unit 45A, a second filter coefficient updating unit 45B, a first adaptive filter 47A, and a second adaptive filter 47B.

The standard signal generating unit 41 calculates a vibration frequency based on engine rotation speed information, and also generates a standard signal correlated with the calculated vibration frequency. The standard signal generated at the standard signal generating unit 41 actually is generated as a cosine wave signal and a sine wave signal.

The first reference signal generating unit 43A generates a first reference signal R1 where the standard signal has been corrected, based on the standard signal generated at the standard signal generating unit 41 and the first transfer function C1 acquired by prediction beforehand. The second reference signal generating unit 43B generates a second reference signal R2 where the standard signal has been corrected, based on the standard signal generated at the standard signal generating unit 41 and the second transfer function C2 acquired by prediction beforehand.

The first filter coefficient updating unit 45A updates a filter coefficient W1 of the first adaptive filter 47A by performing computation in which the first reference signal R1 generated at the first reference signal generating unit 43A, the error signal e1 relating to sound collected by the first microphone 13A, the first transfer function C1, and a step-size parameter M1 set at the time of adjusting operation stability of the first adaptive filter 47A, are substituted into a computation expression (see Expression 1) of a least mean square (LMS) adaptive algorithm.

$$W1_{n+1} = W1_n - R1 \times e1 \times C1 \times M1 \qquad \text{(Expression 1)}$$

In the same way, the second filter coefficient updating unit 45B updates a filter coefficient W2 of the second adaptive filter 47B by performing computation in which the second reference signal R2 generated at the second reference signal generating unit 43B, the error signal e2 relating to sound collected by the second microphone 15A, the second transfer function C2, and a step-size parameter M2 set at the time of adjusting operation stability of the second adaptive filter 47B, are substituted into a computation expression (see Expression 2) of a least mean square (LMS) adaptive algorithm.

$$W2_{n+1}=W2_n-R2\times e2\times C2\times M2 \quad \text{(Expression 2)}$$

The first and second filter coefficient updating units 45A, 45B set the step-size parameter M1, M2 in accordance with the composite mode section information. More specifically, in a case where the compounded sound output mode is selected, the first filter coefficient updating unit 45A sets the step-size parameter M1 to a value smaller as compared to a case where the cancellation sound output mode has been selected. In the same way, in a case where the compounded sound output mode is selected, the second filter coefficient updating unit 45B sets the step-size parameter M2 to a value smaller as compared to a case where the cancellation sound output mode has been selected. This is to proactively avoid a situation in the compounded sound output mode where control operations of active noise reduction become unstable due to the filter coefficients W1 and W2 of the first and second adaptive filters 47A and 47B being updated in accordance with the sound collection results related to the first and second composite audios (error signals).

The first adaptive filter 47A generates control signals relating to the first cancellation sound by multiplying the standard signal by the filter coefficient W1. In the same way, the second adaptive filter 47B generates control signals relating to the second cancellation sound by multiplying the standard signal by the filter coefficient W2. Examples of the first adaptive filter 47A and second adaptive filter 47B that can be suitably used as appropriate include an adaptive notch filter and a finite impulse response (FIR) filter. The first adaptive filter 47A and the second adaptive filter 47B correspond to a "control signal generating unit" in the present disclosure. The internal configuration of the ANC unit 31 will be described in between description of the active noise reduction devices 17-1 and 17-2 according to the first and second embodiments.

Operations of Vehicular Active Noise Reduction System 11-1 According to First Embodiment Next, operations of the vehicular active noise reduction system 11-1 according to the first embodiment will be described by exemplifying a case where a front-seat passenger in the front-seat space 13 speaks to a back-seat passenger in the back-seat space 15, and a case where a back-seat passenger in the back-seat space 15 speaks to a front-seat passenger in the front-seat space 13. Description will be made assuming that a selection operation has been made to set the composite mode selection switch 25 to the compounded sound output mode.

In the case where a front-seat passenger speaks to a back-seat passenger, first, the conversation voice of the front-seat passenger is collected by the first microphone 13A. The analog error signal e1 relating to the conversation voice of the front-seat passenger collected by the first microphone 13A is input to the third low-pass filter LPF3.

The third low-pass filter LPF3 passes audio signals of the frequency bands of the analog error signals e1 relating to the conversation voice of the front-seat passenger collected by the first microphone 13A that are lower than a cutoff frequency (e.g., 200 Hz). The analog error signals e1 following low-pass filter processing at the third low-pass filter LPF3 are input to the first A/D converter AD1 (which will be described later) and the first high-pass filter HPF1.

The first high-pass filter HPF1 passes audio signals of the frequency bands of the analog error signals e1 that have been subjected to low-pass filter processing at the third low-pass filter LPF3 that are higher than a cutoff frequency (e.g., 200 Hz). This removes sound component belonging to the frequency band lower than the cutoff frequency (i.e., the gain of this sound component is attenuated). The frequency bands of the sound component thus removed are in common with the frequency bands of noise which the ANC unit 31 reduces (including engine noise). Accordingly, a situation where the gain of frequency bands relating to noise is diffused is avoided proactively, and control operations of active noise reduction can be stabilized.

The analog error signals e1 following high-pass filter processing at the first high-pass filter HPF1 are input to the third A/D converter AD3. The third A/D converter AD3 converts the analog error signals e1 following high-pass filter processing at the first high-pass filter HPF1 into digital error signals e1. The converted digital error signals e1 are input to the ACP control unit 33-1 via the transfer function acquisition unit 32.

The ACP control unit 33-1 corrects the converted digital error signals e1 by multiplying by the gain coefficient G2 set so that the open-loop transfer function is 0 dB (1 times) or smaller at all frequency bands. Accordingly, stabilizing the control operations of active noise reduction enables a situation where howling occurs to be proactively avoided. After correction at the ACP control unit 33-1, the digital error signals e1 relating to conversation voice of the front-seat passenger are input to the second audio compositing unit 37.

On the other hand, the analog error signals e2 relating to noise occurring at the back-seat space 15 that has been collected by the second microphone 15A are input to the fourth low-pass filter LPF4, to realize active noise reduction at the back-seat space 15. The fourth low-pass filter LPF4 passes audio signals of the frequency bands of the analog error signals e2 relating to the noise occurring at the back-seat space 15 collected by the second microphone 15A that are lower than a cutoff frequency (e.g., 200 to 500 Hz). The analog error signals e2 following low-pass filter processing at the fourth low-pass filter LPF4 are input to the second A/D converter AD2 and the second high-pass filter HPF2 (which will be described later).

The second A/D converter AD2 converts the analog error signals e2 following low-pass filter processing at the fourth low-pass filter LPF4 into digital error signals e2. The converted digital error signals e2 are input to the second filter coefficient updating unit 45B of the ANC unit 31.

The standard signal generating unit 41 of the ANC unit 31 generates a standard signal correlated with the vibration frequency calculated based on the engine rotation speed information. The second reference signal generating unit 43B generates a second reference signal R2 where the standard signal has been corrected, based on the standard signal generated at the standard signal generating unit 41 and the second transfer function C2 acquired by prediction beforehand.

The second filter coefficient updating unit 45B updates the filter coefficient W2 of the second adaptive filter 47B by performing computation in which the second reference signal R2 generated at the second reference signal generating unit 43B, the error signal e2 relating to noise occurring at the back-seat space 15 that has been collected by the second microphone 15A, the second transfer function C2, and the step-size parameter M2 set at the time of adjusting operation stability of the second adaptive filter 47B, are substituted into the aforementioned Expression 2 and computed.

In a case where the compounded sound output mode is selected, when updating the filter coefficient W2 the second filter coefficient updating unit 45B sets the step-size parameter M2 to a value smaller as compared to a case where the cancellation sound output mode has been selected. This is to proactively avoid a situation in the compounded sound output mode where control operations of active noise reduction become unstable.

The second adaptive filter 47B then generates control signals relating to the second cancellation sound by multiplying the standard signal by the filter coefficient W2. The control signals relating to the second cancellation sound for canceling out noise occurring at the back-seat space 15 are input to the second audio compositing unit 37.

The second audio compositing unit 37 generates the second composite audio where control signals relating to the second cancellation sound for canceling out noise occurring at the back-seat space 15 are composited with the digital error signals e1 relating to the conversation voice of the front-seat passenger after correction at the ACP control unit 33-1. The second composite audio thus generated is input to the second D/A converter DA2.

The second D/A converter DA2 converts the second composite audio generated at the second audio compositing unit 37, that is in digital signal format, into analog signal format. The second composite audio in analog signal format after conversion is input to the second low-pass filter LPF2.

The second low-pass filter LPF2 passes audio signals of the frequency bands of the second composite audio in analog signal format that are lower than a cutoff frequency (e.g., 200 to 500 Hz). The second composite audio in analog signal format following low-pass filter processing at the second low-pass filter LPF2 (error signals e1 relating to conversation voice of front-seat passenger+control signals relating to the second cancellation sound for canceling out noise occurring at the back-seat space 15) is subjected to predetermined amplification at the audio amplifier 19, and then output via the second speaker 15B. The second composite audio in analog signal format that is output via the second speaker 15B includes audio signals of the conversation voice of the front-seat passenger and of the second cancellation sound for canceling out noise occurring at the back-seat space 15. Accordingly, conversation assistance from the front-seat passenger to the back-seat passenger in a closed space, and active noise reduction in the back-seat space 15, both work correctly.

Next, in the case where back-seat passenger speaks to a front-seat passenger, first, the conversation voice of the back-seat passenger is collected by the second microphone 15A. The analog error signal e2 relating to the conversation voice of the back-seat passenger collected by the second microphone 15A is input to the second A/D converter AD2 (which will be described later) and the second high-pass filter HPF2 via the fourth low-pass filter LPF4.

The second high-pass filter HPF2 passes audio signals of the frequency bands of the analog error signals e2 that have been subjected to low-pass filter processing at the fourth low-pass filter LPF4 that are higher than a cutoff frequency (e.g., around 200 to 300 Hz). This removes sound component belonging to the frequency band lower than the cutoff frequency (i.e., the gain of this sound component is attenuated). The frequency bands of the sound component thus removed are in common with the frequency bands of noise which the ANC unit 31 reduces (including engine noise). Accordingly, a situation where the gain of frequency bands relating to noise is reinforced is avoided proactively, and control operations of active noise reduction can be stabilized.

The analog error signals e2 following high-pass filter processing at the second high-pass filter HPF2 are input to the fourth A/D converter AD4. The fourth A/D converter AD4 converts the analog error signals e2 following high-pass filter processing at the second high-pass filter HPF2 into digital error signals e2. The converted digital error signals e2 are input to the ACP control unit 33-1 via the transfer function acquisition unit 32.

The ACP control unit 33-1 multiplies the converted digital error signals e2 by the gain coefficient G1 set so that the open-loop transfer function is 0 dB (1 times) or smaller at all frequency bands. Accordingly, stabilizing the control operations of active noise reduction enables a situation where howling occurs to be proactively avoided. After correction at the ACP control unit 33-1, the digital error signals e2 relating to conversation voice of the back-seat passenger are input to the first audio compositing unit 35.

On the other hand, in order to realize active noise reduction in the front-seat space 13, the analog error signals e1 relating to noise occurring at the front-seat space 13 that has been collected by the first microphone 13A are input to the first A/D converter AD1 and the first high-pass filter HPF1 (which will be described later) via the third low-pass filter LPF3.

The first A/D converter AD1 converts the analog error signals e1 following low-pass filter processing at the third low-pass filter LPF3 into digital error signals e1. The converted digital error signals e1 are input to the first filter coefficient updating unit 45A of the ANC unit 31.

The standard signal generating unit 41 of the ANC unit 31 generates a standard signal correlated with the vibration frequency calculated based on the engine rotation speed information. The first reference signal generating unit 43A generates a first reference signal R1 where the standard signal has been corrected, based on the standard signal generated at the standard signal generating unit 41 and the first transfer function C1 acquired by prediction beforehand.

The first filter coefficient updating unit 45A updates the filter coefficient W1 of the first adaptive filter 47A by performing computation in which the first reference signal R1 generated at the first reference signal generating unit 43A, the error signal e1 relating to noise occurring at the front-seat space 13 that has been collected by the first microphone 13A, the first transfer function C1, and the step-size parameter M1 set at the time of adjusting operation stability of the first adaptive filter 47A, are substituted into the aforementioned Expression 1 and computed.

In a case where the compounded sound output mode is selected, when updating the filter coefficient W1 the first filter coefficient updating unit 45A sets the step-size parameter M1 to a value smaller as compared to a case where the cancellation sound output mode has been selected. This is to proactively avoid a situation in the compounded sound output mode where control operations of active noise reduction become unstable.

The first adaptive filter 47A then generates control signals relating to the first cancellation sound by multiplying the standard signal by the filter coefficient W1. The control signals relating to the first cancellation sound for canceling out noise occurring at the front-seat space 13 are input to the first audio compositing unit 35.

The first audio compositing unit 35 generates the first composite audio where control signals relating to the first cancellation sound for canceling out noise occurring at the front-seat space 13 are composited with the digital error signals e2 relating to the conversation voice of the back-seat passenger after correction at the ACP control unit 33-1. The first composite audio thus generated is input to the first D/A converter DA1.

The first D/A converter DA1 converts the first composite audio generated at the first audio compositing unit 35, that is in digital signal format, into analog signal format. The first composite audio in analog signal format is input to the first low-pass filter LPF1.

The first low-pass filter LPF1 passes audio signals of the frequency bands of the first composite audio in analog signal format that are lower than a cutoff frequency (e.g., around 200 to 300 Hz). The first composite audio in analog signal format following low-pass filter processing at the first low-pass filter LPF1 (error signals e2 relating to conversation voice of back-seat passenger+control signals relating to the first cancellation sound for canceling out noise occurring at the front-seat space 13) is subjected to predetermined amplification at the audio amplifier 19, and then output via the first speaker 13B. The first composite audio in analog signal format that is output via the first speaker 13B includes audio signals of the conversation voice of the back-seat passenger and of the first cancellation sound for canceling out noise occurring at the front-seat space 13. Accordingly, conversation assistance from the back-seat passenger to the front-seat passenger in a closed space, and active noise reduction, both work correctly.

Figure 4:
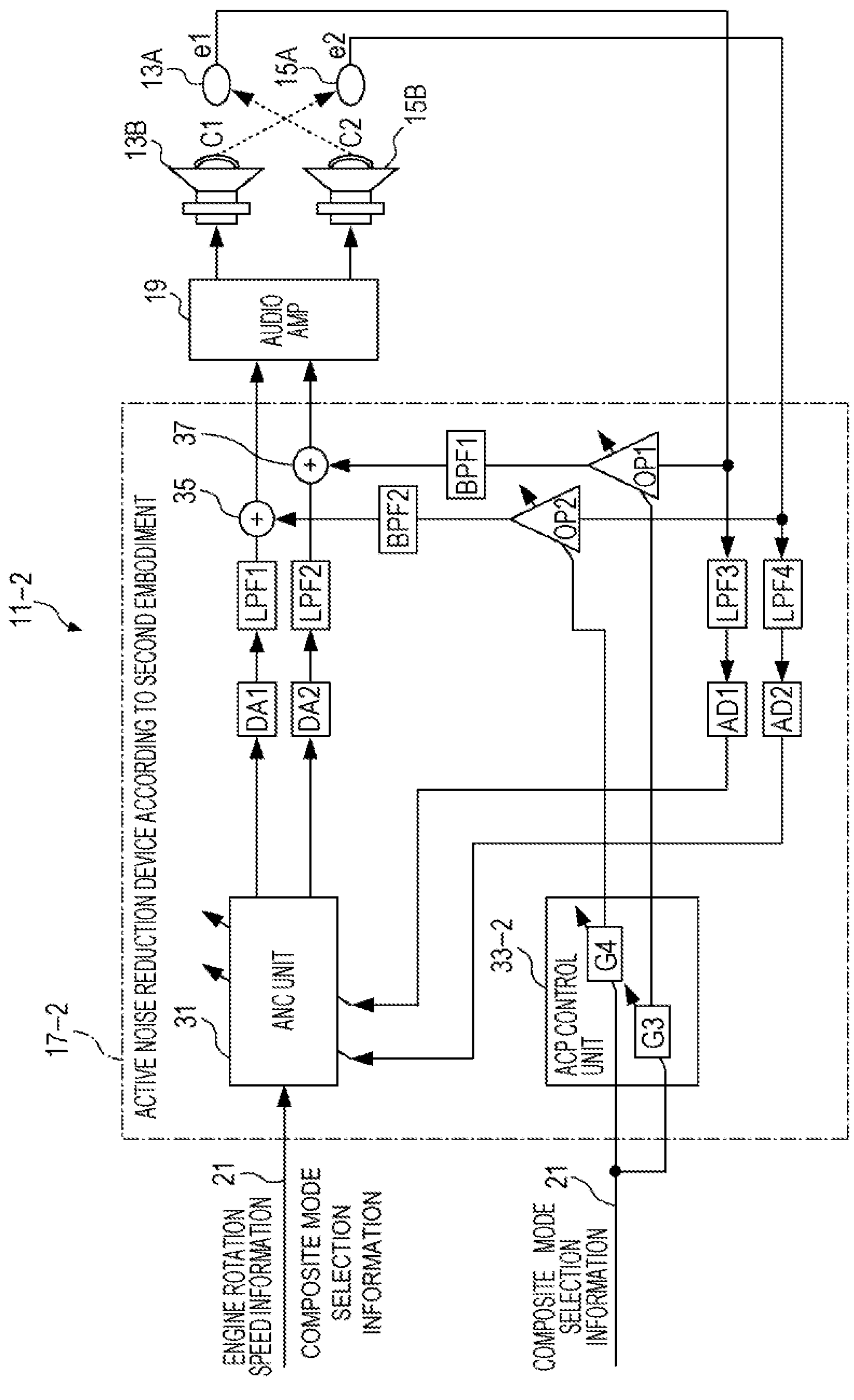
FIG. 4 is a block diagram schematically illustrating the internal configuration of an active noise reduction device according to a second embodiment.

Internal Configuration of Active Noise Reduction Device 17-2 According to Second Embodiment First, the internal configuration of an active noise reduction device 17-2 according to the second embodiment will be described with reference to FIG. 4. FIG. 4 is a block diagram illustrating the schematics of the vehicular active noise reduction system 11-2 according to the second embodiment that has the active noise reduction device 17-2 according to the second embodiment. The active noise reduction device 17-1 according to the first embodiment and the active noise reduction device 17-2 according to the second embodiment have components with common basic functions. Accordingly, instead of describing the configuration of the active noise reduction device 17-2 according to the second embodiment, the points of difference between the first and second embodiments will be noted and these differences will be described.

A configuration is employed in the active noise reduction device 17-2 according to the second embodiment where the analog error signals e1 are amplified to an appropriate gain using a first operational amplifier OP1, while the analog error signals e2 are amplified to an appropriate gain using a second operational amplifier OP2. The amplification processing using the first operational amplifier OP1 and second operational amplifier OP2 is performed by analog signal processing.

The ACP control unit 33-2 of the active noise reduction device 17-2 according to the second embodiment sets gain coefficients G3 and G4, based on composite mode selection information according to the composite mode selection switch 25. The gain of the first operational amplifier OP1 is set based on the gain coefficient G3, and the gain of the second operational amplifier OP2 is set based on the gain coefficient G4. Specifically, in a case where the composite mode selection information indicates an on state (where the audio output mode is the compounded sound output mode), the gains of the first and second operational amplifiers OP1 and OP2 are set to relatively high values (e.g., around 0.7 to 1). On the other hand, in a case where the composite mode selection information indicates an off state (where the audio output mode is the cancellation sound output mode), the gains of the first and second operational amplifiers OP1 and OP2 are set to relatively low values (e.g., around 0 to 0.3).

The active noise reduction device 17-1 according to the first embodiment employs a configuration where frequency bands of audio signals of the error signals e1, relating to conversation voice at the front-seat space 13 collected by the first microphone 13A, higher than a cutoff frequency (e.g., around 200 to 300 Hz), are passed using the first high-pass filter HPF1, in order to remove sound components having the frequency bands of noise (including engine noise) which the ANC unit 31 reduces (i.e., the gain of this sound component is attenuated), from the error signals e1. In this configuration, frequency bands of audio signals of the error signals e2, relating to conversation voice at the back-seat space 15 collected by the second microphone 15A, higher than the cutoff frequency (e.g., around 200 to 300 Hz), are passed using the second high-pass filter HPF2, in order to remove sound components having the frequency bands of noise (including engine noise) which the ANC unit 31 reduces (i.e., the gain of this sound component is attenuated), from the error signals e2.

In comparison with this, the active noise reduction device 17-2 according to the second embodiment employs a configuration where audio signals of the analog error signals e1 relating to conversation voice recorded by the first microphone 13A in the front-seat space 13 and then subjected to amplification processing at the first operational amplifier OP1, that belong to a predetermined frequency bandwidth, are passed using a first band-pass filter BPF1, in order to remove sound components having the frequency bands of noise (including engine noise) which the ANC unit 31 reduces (i.e., the gain of this sound component is attenuated), from the error signals e1. In this configuration, audio signals of the analog error signals e2 relating to conversation voice recorded by the second microphone 15A in the back-seat space 15 and then subjected to amplification processing at the second operational amplifier OP2, that belong to a predetermined frequency bandwidth, are passed using a second band-pass filter BPF2, in order to remove sound components having the frequency bands of noise (including engine noise) which the ANC unit 31 reduces (i.e., the gain of this sound component is attenuated), from the error signals e2. Note that the band-pass filter processing using the first band-pass filter BPF1 and the second band-pass filter BPF2 is performed by analog signal processing.

The analog error signals e1 after amplification processing at the first band-pass filter BPF1 are input to the second audio compositing unit 37. On the other hand, the analog error signals e2 after amplification processing at the second band-pass filter BPF2 are input to the first audio compositing unit 35.

Operations of Vehicular Active Noise Reduction System 11-2 According to Second Embodiment Next, operations of the vehicular active noise reduction system 11-2 according to the second embodiment will be described by exemplifying a case where a front-seat passenger in the front-seat space 13 speaks to a back-seat passenger in the back-seat space 15, and a case where a back-seat passenger in the back-seat space 15 speaks to a front-seat passenger in the front-seat space 13. Description will be made assuming that the composite mode selection switch 25 has been set to compounded sound output mode (i.e., the composite mode selection information indicates an on state).

In the case where a front-seat passenger speaks to a back-seat passenger, first, the conversation voice of the front-seat passenger is collected by the first microphone 13A. The analog error signal e1 relating to the conversation voice of the front-seat passenger collected by the first microphone 13A is input to the first operational amplifier OP1 and the third low-pass filter LPF3.

The first operational amplifier OPT amplifies the analog error signals e1 relating to the conversation voice of the front-seat passenger collected by the first microphone 13A, based on the gain coefficient G3 set at the ACP control unit 33-2. The analog error signals e1 amplified at the first operational amplifier OP1 are input to the first band-pass filter BPF1.

The first band-pass filter BPF1 passes audio signals of the analog error signals e1 following amplification processing at the first operational amplifier OP1, belonging to a predetermined frequency bandwidth. This removes sound component of the frequency band of noise (including engine noise) which the ANC unit 31 reduces (i.e., the gain of this sound component is attenuated). The analog error signals e1 relating to the conversation voice of the front-seat passenger, following the band-pass filter processing at the first band-pass filter BPF1, are input to the second audio compositing unit 37.

On the other hand, the analog error signals e2 relating to noise occurring at the back-seat space 15 that has been collected by the second microphone 15A are input to the fourth low-pass filter LPF4, to realize active noise reduction at the back-seat space 15. The fourth low-pass filter LPF4 passes audio signals of the frequency bands of the analog error signals e2 relating to the noise occurring at the back-seat space 15 collected by the second microphone 15A that are lower than a cutoff frequency (e.g., 200 to 500 Hz). The analog error signals e2 following low-pass filter processing at the fourth low-pass filter LPF4 are input to the second A/D converter AD2.

The second A/D converter AD2 converts the analog error signals e2 following low-pass filter processing at the fourth low-pass filter LPF4 into digital error signals e2. The converted digital error signals e2 are input to the ANC unit 31.

The ANC unit 31 generates control signals relating to the second cancellation sound for canceling out noise occurring at the back-seat space 15, based on the standard signal correlated with the vibration frequency calculated based on the engine rotation speed information, the digital error signals e2, and so forth. The control signals relating to the second cancellation sound thus generated are input to the second D/A converter DA2.

The second D/A converter DA2 converts the control signals relating to the second cancellation sound in digital signal format into analog signal format. The control signals relating to the second cancellation sound in analog signal format after conversion are input to the second low-pass filter LPF2.

The second low-pass filter LPF2 passes audio signals of the frequency bands of the control signals relating to the second cancellation sound in analog signal format that are lower than a cutoff frequency (e.g., 200 to 500 Hz). The control signals relating to the second cancellation sound for canceling out noise occurring at the back-seat space 15 are input to the second audio compositing unit 37 after the low-pass filter processing at the second low-pass filter LPF2.

The second audio compositing unit 37 generates the second composite audio where control signals relating to the second cancellation sound for canceling out noise occurring at the back-seat space 15 (the output of the second low-pass filter LPF2), generated by the ANC unit 31 in analog signal format, are composited with the analog error signals e1 (the output of the first band-pass filter BPF1) relating to the conversation voice of the front-seat passenger. The second composite audio (error signals e1 relating to conversation voice of front-seat passenger+control signals relating to the second cancellation sound for canceling out noise occurring at the back-seat space 15) is subjected to predetermined amplification at the audio amplifier 19, and then output via the second speaker 15B. The second composite audio in analog signal format that is output via the second speaker 15B includes audio signals of the conversation voice of the front-seat passenger and of the second cancellation sound for canceling out noise occurring at the back-seat space 15. Accordingly, conversation assistance from the front-seat passenger to the back-seat passenger in a closed space, and active noise reduction, both work correctly.

In the case where a back-seat passenger speaks to a front-seat passenger, first, the conversation voice of the back-seat passenger is collected by the second microphone 15A. The analog error signals e2 relating to the conversation voice of the back-seat passenger collected by the second microphone 15A are input to the second operational amplifier OP2 and the fourth low-pass filter LPF4.

The second operational amplifier OP2 amplifies the analog error signals e2 relating to the conversation voice of the back-seat passenger collected by the second microphone 15A, based on the gain coefficient G4 set at the ACP control unit 33-2. The analog error signals e2 amplified at the second operational amplifier OP2 are input to the second band-pass filter BPF2.

The second band-pass filter BPF2 passes audio signals of the analog error signals e2 following amplification processing at the second operational amplifier OP2, belonging to a predetermined frequency bandwidth. This removes sound component of the frequency band of noise (including engine noise) which the ANC unit 31 reduces (i.e., the gain of this sound component is attenuated). The analog error signals e2 relating to the conversation voice of the back-seat passenger, following the band-pass filter processing at the second band-pass filter BPF2, are input to the first audio compositing unit 35.

On the other hand, the analog error signals e1 relating to noise occurring at the front-seat space 13 that has been collected by the first microphone 13A are input to the third low-pass filter LPF3, to realize active noise reduction at the front-seat space 13. The third low-pass filter LPF3 passes audio signals of the frequency bands of the analog error signals e1 relating to the noise occurring at the front-seat space 13 collected by the first microphone 13A that are lower than a cutoff frequency (e.g., around 200 to 500 Hz). The analog error signals e1 following low-pass filter processing at the third low-pass filter LPF3 are input to the first A/D converter AD1.

The first A/D converter AD1 converts the analog error signals e1 following low-pass filter processing at the third low-pass filter LPF3 into digital error signals e1. The converted digital error signals e1 are input to the ANC unit 31.

The ANC unit 31 generates control signals relating to the first cancellation sound for canceling out noise occurring at the front-seat space 13, based on the standard signal correlated with the vibration frequency calculated based on the engine rotation speed information, the digital error signal e1, and so forth. The control signals relating to the first cancellation sound thus generated are input to the first D/A converter DA1.

The first D/A converter DA1 converts the control signals relating to the first cancellation sound in digital signal format into analog signal format. The control signals relating to the first cancellation sound in analog signal format after conversion are input to the first low-pass filter LPF1.

The first low-pass filter LPF1 passes audio signals of the frequency bands of the control signals relating to the first cancellation sound in analog signal format that are lower than a cutoff frequency (e.g., around 200 to 500 Hz). The control signals relating to the first cancellation sound for canceling out noise occurring at the front-seat space 13 are input to the first audio compositing unit 35 after the low-pass filter processing at the first low-pass filter LPF1.

The first audio compositing unit 35 generates the first composite audio where control signals relating to the first cancellation sound for canceling out noise occurring at the front-seat space 13 (the output of the first low-pass filter LPF1), generated by the ANC unit 31 in analog signal format, are composited with the analog error signals e2 (the output of the second band-pass filter BPF2) relating to the conversation voice of the back-seat passenger. The first composite audio thus generated is subjected to predetermined amplification at the audio amplifier 19, and then output via the first speaker 13B. The first composite audio in analog signal format that is output via the first speaker 13B includes audio signals of the conversation voice of the back-seat passenger and of the first cancellation sound for canceling out noise occurring at the front-seat space 13. Accordingly, conversation assistance from the back-seat passenger to the front-seat passenger in a closed space, and active noise reduction, both work correctly.

Operation and Effect of Vehicular Active Noise Reduction System 11

Next, the operations and effects of the vehicular active noise reduction system 11 will be described. The active noise reduction device 17 of the vehicular active noise reduction system 11 according to the embodiments of the present disclosure includes the first audio compositing unit 35 that generates the first composite audio where audio signals of the first cancellation sound, generated by referencing noise, and audio (error signals e1) collected by the first microphone (first sound collecting unit) 13A, are composited with audio (error signals e2) collected by the second microphone (second sound collecting unit) 15A, and the second audio compositing unit 37 that generates the second composite audio where audio signals of a second cancellation sound generated by referencing noise, and audio collected by the second microphone (second sound collecting unit) 15A, are composited with audio collected by the first microphone (first sound collecting unit) 13A. The active noise reduction device 17 effects control to output the first composite audio to the first speaker (first sound output unit) 13B, while outputting the second composite audio to the second speaker (second sound output unit) 15B, and at the time of generating the first and second composite audios, performs processing to remove audio components, belonging to the frequency band relating to noise that is to be reduced in the closed space (in the vehicle cabin), from each of the audio collected by the first microphone 13A and the audio collected by the second microphone 15A. Thus, according to the vehicular active noise reduction system 11 of the embodiments according to the present disclosure, conversation assistance from the back-seat passenger to the front-seat passenger in the vehicle cabin, and active noise reduction, both work correctly.

With the vehicular active noise reduction system 11-1 according to the first embodiment, a conventional active noise reduction device that reduces noise occurring in the vehicle cabin is further provided with the composite mode selection switch 25, ACP control unit 33-1, first audio compositing unit 35, second audio compositing unit 37, switching unit 39, first high-pass filter HPF1, second high-pass filter HPF2, third A/D converter AD3, and fourth A/D converter AD4, whereby a conversation assistance function of assisting smooth conversation in the vehicle cabin can be implemented relatively easily.

With the vehicular active noise reduction system 11-2 according to the second embodiment, a conventional active noise reduction device that reduces noise occurring in the vehicle cabin is further provided with the composite mode selection switch 25, ACP control unit 33-2, first audio compositing unit 35, second audio compositing unit 37, first operational amplifier OP1, second operational amplifier OP2, first band-pass filter BPF1, and second band-pass filter BPF2, whereby a conversation assistance function of assisting smooth conversation in the vehicle cabin can be implemented relatively easily.

Also, the active noise reduction device 17-1 according to the first embodiment may employ a configuration including the transfer function acquisition unit 32 that acquires open-loop transfer functions of an acoustics system configured including the active noise reduction device 17-1, first speaker (first sound output unit) 13B and second speaker (second sound output unit) 15B, first microphone (first sound collecting unit) 13A and second microphone (second sound collecting unit) 15A, and audio amplifier 19 (although the audio amplifier 19 may be omitted), the ACP control unit (setting unit) 33-1 that sets gain coefficients G1 and G2 so that the open-loop transfer function acquired by the transfer function acquisition unit 32 is 0 dB (1 times) or smaller (preferably at all frequency bands), and the ACP control unit (correction unit) 33-1 that performs correction by multiplying the error signal e1, relating to the conversation voice of the passenger in the front seat collected by the first microphone 13A, by the gain coefficient G2 set as described above, and also performs correction by multiplying the error signal e2, relating to the conversation voice of the passenger in the back seat collected by the second microphone 15A, by the gain coefficient G1 set as described above.

According to this configuration, the ACP control unit 33-1 performs correction of the error signals e1 relating to the conversation voice of the front-seat passenger collected by the first microphone 13A, by multiplying by the gain coefficient G2 that has been set, and performs correction of the error signals e2 relating to the conversation voice of the back-seat passenger collected by the second microphone 15A, by multiplying by the gain coefficient G1 that has been set. Accordingly, stabilizing the control operations of active noise reduction enables a situation where howling occurs to be proactively avoided, and conversation assistance from the back-seat passenger to the front-seat passenger in a closed space and active noise reduction both work correctly.

The active noise reduction device 17 may switchably have, as audio output modes used to output sound from at least one of the first speaker (first sound output unit) 13B and second speaker (second sound output unit) 15B, the compounded sound output mode where the first composite audio is output to the first speaker 13B while the second composite audio is output to the second speaker 15B, and the cancellation sound output mode where a first or second cancellation sound is output from at least one of the first speaker 13B and the second speaker 15B. The active noise reduction device 17 may employ a configuration including reference signal generating units 43A and 43B that generate reference signals based on a standard signal correlated at least with noise, filter coefficient updating units 45A and 45B that update filter coefficients W1 and W2 of the adaptive filters 47A and 47B using the reference signals R1 and R2 generated at the reference signal generating units 43A and 43B, the error signals (e1 or e2) related to sound collected by the first microphone 13A or the second microphone 15A, and the step-size parameters M1 and M2 set at the time of adjusting the coefficient updating amount of the adaptive filters 47A and 47B, and the adaptive filters (control signal generating units) 47A and 47B that generate control signals relating to the first or second cancellation sounds by multiplying the standard signal by the filter coefficients W1 and W2 of the adaptive filters 47A and 47B. The values set to the step-size parameters M1 and M2 in a case where the compounded sound output mode is selected may be smaller as compared to a case where the cancellation sound output mode is selected.

According to this configuration, stability of control operations relating to active noise reduction when updating the filter coefficients of the adaptive filters 47A and 47B can be ensured, regardless of which of the compounded sound output mode and cancellation sound output mode is selected as the audio output mode.

A configuration may be employed where the ACP control unit 33-1 of the active noise reduction device 17-1 according to the first embodiment sets a value larger than 0 but smaller than 1 as the gain coefficient in a case where the compounded sound output mode is selected, and on the other hand set 0 as the gain coefficient in a case where the cancellation sound output mode is selected, with switching from one of the compounded sound output mode or cancellation sound output mode to the other audio output mode being performed according to a predetermined time constant.

According to this configuration, in a case where the compounded sound output mode is selected, correction is performed where the error signals (e1 or e2) relating to sound collected at the first microphone 13A or second microphone 15A are multiplied by a value larger than 0 but smaller than 1 as the gain coefficient. In this case, the influence of error signals can be suppressed. On the other hand, in a case where the cancellation sound output mode is selected, correction is performed where the error signals (e1 or e2) relating to sound collected at the first microphone 13A or second microphone 15A are multiplied by 0 as the gain coefficient. In this case, the influence of error signals can be eliminated.

Also, switching from one of the compounded sound output mode or cancellation sound output mode to the other audio output mode is performed according to a predetermined time constant, so even in a case where the gain coefficients are switched in accordance with switching of the audio output mode, for example, occurrence of abnormal noise, which would occur in a case of having instantaneously (i.e., without a predetermined time constant) switched the audio output mode, can be suppressed. As described above, according to the vehicular active noise reduction system 11 according embodiments of the present disclosure, stability of control in the vehicular active noise reduction system 11 can be ensured at all frequency bands, regardless of which of the compounded sound output mode and cancellation sound output mode is selected as the audio output mode.

Also, the vehicular active noise reduction system 11-2 according to the second embodiment of the present disclosure generates the first composite audio by compositing the first cancellation sound audio signals with the analog error signals e2 unchanged from the analog signal format (and generates the second composite audio by compositing the second cancellation sound audio signals with the analog error signals e1 unchanged from the analog signal format), so the advantage of being able to clearly communicate the voice of a passenger in one of the front seat and back seat to a passenger in the other can be expected, regardless of the computation processing capabilities (sampling time) of the active noise reduction device 17-2. The reason is that generally, when converting analog audio signals in to digital audio signals, components necessary to recognize the voice of the passenger as speech may be missing from the output (quantization error or quantization distortion) if the computation processing capabilities of the control device such as the microcomputer or the like are low. On the other hand, such trouble can be proactively prevented in the case according to the second embodiment.

Particularly, the vehicular active noise reduction system 11-2 according to the second embodiment of the present disclosure performs cutoff processing of frequency bands relating to noise (including engine noise) which is the object of reduction by the ANC unit 31, using band-pass filters, so while ensuring stability of active noise reduction control, audio components of bands outside of the frequency band of the conversation voices of passengers are cut off as appropriate. As a result, the advantage of being able to communicate passenger voices even more clearly can be expected.

Other Embodiments

The above-described embodiments are but specific examples of the present disclosure. Accordingly, the technical scope of the present disclosure should not be restrictively interpreted according to the embodiments. The present disclosure can be carried out in various forms without departing from the essence or principal features thereof.

For example, although engine noise has been exemplified as noise in the vehicle cabin in the description of the embodiments of the present disclosure, the present disclosure is not restricted to this example. The present disclosure is applicable to noise in general in the vehicle cabin, including road noise (sound generated by the tires on the pavement) and drumming noise (sound generated by the roof panel or floor panel vibrating while driving) for example, besides engine noise.

Although around 200 to 500 Hz has been exemplified as the cutoff frequency set to the first low-pass filter LPF1, second low-pass filter LPF2, third low-pass filter LPF3, and fourth low-pass filter LPF4 in the description of the embodiments of the present disclosure, the present disclosure is not restricted to this example. Appropriate values may be set as the cutoff frequency set to each of the first low-pass filter LPF1, second low-pass filter LPF2, third low-pass filter LPF3, and fourth low-pass filter LPF4, taking into consideration the vehicular active noise reduction system 11 according to the embodiments of the present disclosure delivering sufficient performance.

Although around 200 to 300 Hz has been exemplified as the cutoff frequency set to the first high-pass filter HPF1 and second high-pass filter HPF2 in the description of the embodiments of the present disclosure, the present disclosure is not restricted to this example. Appropriate values may be set as the cutoff frequency set to each of the first high-pass filter HPF1 and second high-pass filter HPF2, taking into consideration the vehicular active noise reduction system 11 according to the embodiments of the present disclosure delivering sufficient performance.

Although the active noise reduction system according to the present disclosure has been exemplified as being implemented in the cabin space of a vehicle in the description of the embodiments of the present disclosure, the present disclosure is not restricted to this example. The active noise reduction system according to the present disclosure is applicable to cabin spaces in aircraft, cabin spaces in railway cars, and so forth, for example.

Although an arrangement has been described where one speaker (first speaker 13B) is disposed in the front-seat space 13 in the vehicle cabin, in the description of the embodiments of the present disclosure, the present disclosure is not restricted to this example. The vehicular active noise reduction system 11 according to the embodiments of the present disclosure may employ a configuration where speakers are provided at both the driver's seat side and the passenger's seat side of the front-seat space 13, for example. Assumption will be made that an automotive navigation device is installed in the vehicle V having this configuration, for guiding a route to a destination by images and sound. In this case, the audio for guidance by the navigation device is output from the speaker at the driver's side. Also, a configuration may be employed where the audio output mode of the active noise reduction system to which the speaker at the driver's side belongs is switched from the composite audio output mode to the cancellation sound output mode, so that no sound from the back-seat space 15 is output from the driver's side speaker while the guidance audio is being output from the navigation device.

Although an arrangement has been described where the audio output mode is switched to one of the compounded sound output mode and cancellation sound output mode based on composite mode selection information selected by operation of the composite mode selection switch 25 by a passenger in the description of the embodiments of the present disclosure, the present disclosure is not restricted to this example. A configuration may be employed where switching of the audio output mode is performed in accordance with the state of the vehicle or external disturbance (noise). Specifically, a configuration may be employed where the audio output mode is switched from compounded sound output mode to cancellation sound output mode in a case where control operations relating to active noise reduction are unstable (e.g., a state where collection at the microphone exhibits a tendency of positive feedback).

Although the transfer function acquisition unit 32 that acquires open-loop transfer functions as the overall acoustics system has been exemplified in the description of the embodiments of the present disclosure as being configured as a function unit (software) which the active noise reduction device (microcomputer) 17 has, the present disclosure is not restricted to this example. A configuration may be employed where open-loop transfer functions are acquired by storing open-loop transfer functions for the overall acoustics system, measured using measurement instruments and the design stage.

Although an example of using the first and second band-pass filters BPF1 and BPF2 to remove audio signal components of the frequency band relating to noise (including engine noise), which is to be reduced by the ANC unit 31, has been described regarding the second embodiment of the present disclosure, the present disclosure is not restricted to this example. High-pass filters capable of removing audio signal components of the frequency band relating to noise to be reduced may be employed instead of the first and second band-pass filters BPF1 and BPF2. Although a specific form of embodiment has been described above and illustrated in the accompanying drawings in order to be more clearly understood, the above description is made by way of example and not as limiting the scope of the invention defined by the accompanying claims. The scope of the invention is to be determined by the accompanying claims. Various modifications apparent to one of ordinary skill in the art could be made without departing from the scope of the invention. The accompanying claims cover such modifications.

What is claimed is:

1. An active noise reduction system that actively reduces noise, the system comprising:

a first sound collecting unit disposed in a first space in a closed space, that collects sound generated in the first space;

a second sound collecting unit disposed in a second space situated away from the first space in the closed space, that collects sound generated in the second space;

a first sound output unit that is disposed in the first space and outputs sound;

a second sound output unit that is disposed in the second space and outputs sound; and an active noise reduction device that performs control to output a cancellation sound that reduces noise in the closed space, from at least one of the first sound output unit and the second sound output unit, the active noise reduction device including:

a first audio compositing unit that generates first composite audio generated by compositing audio signals of a first cancellation sound with audio collected by the second sound collecting unit, the first cancellation sound being generated by referencing the noise and audio collected by the first sound collecting unit, and a second audio compositing unit that generates second composite audio generated by compositing audio signals of a second cancellation sound with audio collected by the first sound collecting unit, the second cancellation sound being generated by referencing the noise and audio collected by the second sound collecting unit, wherein the active noise reduction device performs control to output the first composite audio to the first sound output unit, while outputting the second composite audio to the second sound output unit, and at the time of generating the first and second composite audios, performs processing to remove audio components from each of the audio collected by the first sound collecting unit and the audio collected by the second sound collecting unit, the audio components belonging to a frequency band associated with noise that is to be reduced in the closed space.

2. The active noise reduction system according to claim 1, wherein the active noise reduction device further includes a transfer function acquisition unit that acquires an open-loop transfer function of an acoustics system configured including the active noise reduction device, the first sound output unit and the second sound output unit, and the first sound collecting unit and the second sound collecting unit, a setting unit that sets a gain coefficient so that the open-loop transfer function acquired by the transfer function acquisition unit is 0 dB or smaller, and a correction unit that performs correction by multiplying the gain coefficient set by the setting unit to each of error signals associated with sound collected at the first sound collecting unit and the second sound collecting unit, respectively.

3. The active noise reduction system according to claim 2, wherein the active noise reduction device switchably has, as audio output modes used to output sound from at least one of the first sound output unit and the second sound output unit, a compounded sound output mode where the first composite audio is output to the first sound output unit while the second composite audio is output to the second sound output unit, and a cancellation sound output mode where the first cancellation sound is output from the first sound output unit, or the second cancellation sound is output from the second sound output unit, or both the active noise reduction device further including a reference signal generating unit that generates a reference signal using a standard signal correlated at least with the noise, a filter coefficient updating unit that updates a filter coefficient of an adaptive filter, using the reference signal generated at the reference signal generating unit, error signals associated with sound collected by the first sound collecting unit or sound collected by the second sound collecting unit, and a step-size parameter set when adjusting operation stability of the adaptive filter, and a control signal generating unit that generates control signals associated with the first or second cancellation sounds by multiplying the standard signal by the filter coefficient of the adaptive filter, wherein a value set to the step-size parameter in a case where the compounded sound output mode is selected is smaller than the value set in a case where the cancellation sound output mode is selected.

4. The active noise reduction system according to claim 3, wherein the active noise reduction device sets a value larger than 0 but smaller than 1 as the gain coefficient in a case where the compounded sound output mode is selected, and on the other hand set 0 as the gain coefficient in a case where the cancellation sound output mode is selected, wherein switching from one of the compounded sound output mode and the cancellation sound output mode to the other audio output mode is performed according to a predetermined time constant.

5. The active noise reduction system according to claim 3, wherein the standard signal is correlated with a vibration frequency of the noise.

6. The active noise reduction system according to claim 3, wherein the filter coefficient updating unit updates the filter coefficient of the adaptive filter in accordance with the following equation:

$$W_{n+1}=W_n-R\times e\times C\times M$$

wherein W is the filter coefficient, R is the reference signal, e is the error signal associated with sound collected by the first sound collecting unit or the second sound collecting unit, C is a transfer function corresponding to a path from the first sound output unit to the second sound collecting unit or a path from the second sound output unit to the first sound collecting unit, and M is the step-size parameter.

7. A vehicle active noise reduction system that actively reduces noise, the system comprising:

a first sound collecting unit, disposed in a front-seat space in a cabin of a vehicle, that collects sound generated in the front-seat space;

a second sound collecting unit, disposed in a back-seat space situated in the cabin, that collects sound generated in the back-seat space;

a first sound output unit that is disposed in the front-seat space and outputs sound;

a second sound output unit that is disposed in the back-seat space and outputs sound; and an active noise reduction device that performs control to output a cancellation sound that reduces noise in the cabin, from at least one of the first sound output unit and the second sound output unit, the active noise reduction device including a first audio compositing unit that generates first composite audio generated by compositing audio signals of a first cancellation sound with audio collected by the second sound collecting unit, the first cancellation sound being generated by referencing the noise and audio collected by the first sound collecting unit, and a second audio compositing unit that generates second composite audio generated by compositing audio signals of a second cancellation sound with audio collected by the first sound collecting unit, the second cancellation sound being generated by referencing the noise and audio collected by the second sound collecting unit, wherein the active noise reduction device performs control to output the first composite audio to the first sound output unit, while outputting the second composite audio to the second sound output unit, and at the time of generating the first and second composite audios, performs processing to remove audio components from each of the audio collected by the first sound collecting unit and the audio collected by the second sound collecting unit, the audio components belonging to a frequency band associated with noise that is to be reduced in the cabin.

8. A vehicle active noise reduction apparatus that actively reduces noise, comprising:

a first microphone, disposed in a front-seat space in a cabin of a vehicle, that collects sound generated in the front-seat space;

a second microphone, disposed in a back-seat space situated in the cabin, that collects sound generated in the back-seat space;

a first speaker that is disposed in the front-seat space and outputs sound;

a second speaker that is disposed in the back-seat space and outputs sound; and an active noise reduction computer configured to perform control to output a cancellation sound that reduces noise in the cabin, from at least one of the first speaker and the second speaker, the active noise reduction computer is configured to perform:

a first audio compositing unit that generates first composite audio generated by compositing audio signals of a first cancellation sound with audio collected by the second microphone, the first cancellation sound being generated by referencing the noise and audio collected by the first microphone, and a second audio compositing unit that generates second composite audio generated by compositing audio signals of a second cancellation sound with audio collected by the first microphone, the second cancellation sound being generated by referencing the noise and audio collected by the second microphone, wherein the active noise reduction computer is configured to:

perform control to output the first composite audio to the first speaker, while outputting the second composite audio to the second speaker, and at the time of generating the first and second composite audios, perform processing to remove audio components from each of the audio collected by the first microphone and the audio collected by the second microphone, the audio components belonging to a frequency band associated with noise that is to be reduced in the cabin.

* * * * *